US00PP15042P2

(12) United States Plant Patent
Utecht

(10) Patent No.: US PP15,042 P2
(45) Date of Patent: Jul. 27, 2004

(54) GERANIUM PLANT NAMED 'FISROLAV'

(50) Latin Name: *Pelargonium zonale*
Varietal Denomination: Fisrolav

(75) Inventor: Angelika Utecht, Montabaur (DE)

(73) Assignee: Florfis AG, Binnengen (CH)

( * ) Notice: Subject to any disclaimer, the term of this patent is extended or adjusted under 35 U.S.C. 154(b) by 0 days.

(21) Appl. No.: 10/715,495

(22) Filed: Nov. 19, 2003

(51) Int. Cl.[7] ..... A01H 5/00

(52) U.S. Cl. ..... Plt./329

(58) Field of Search ..... Plt./329, 325, 328

*Primary Examiner*—Kent Bell
(74) *Attorney, Agent, or Firm*—Foley & Lardner LLP

(57) ABSTRACT

A new and distinct cultivar of geranium plant named 'Fisrolav', particularly characterized by the combined features of lavender-pink colored, semi-double flowers with small white eyes, long peduncles, relatively large, medium-green leaves with weak zonation, vigorous growth, low and wide plant habit, and medium to late spring flowering response.

1 Drawing Sheet

Genus and species of the invention: Hybrid *Pelargonium zonale* L'Héritier.
Variety denomination: 'Fisrolav'.

BACKGROUND OF THE INVENTION

The present invention comprises a new and distinct cultivar of geranium, botanically known as *Pelargonium zonale*, and hereinafter referred to by the cultivar name 'Fisrolav'.

'Fisrolav' is a product of a planned breeding program which had the objective of creating new zonal geranium cultivars with cultivars with semi-double flowers, relatively vigorous, but well-branched growth habit, good outdoor performance, and in various flower colors.

'Fisrolav' originated from a hybridization made by the inventor, Angelika Utecht, in a controlled breeding program in Hillscheid, Germany, in 1998. The female parent was an unpatented hybrid seedling, no. K96-0827-2, having light violet, semi-double flowers, dark-green foliage with distinct zonation, and moderately compact growth. The male parent of 'Fisrolav' was the unpatented hybrid seedling no. K93-1030-1, with single-type, light violet flowers, dark-green leaves with weak zonation, and relatively strong growth.

'Fisrolav' was selected as one flowering plant within the progeny of the stated cross by Angelika Utecht in 1999, in a controlled environment in Moncarapacho, Portugal.

The first act of asexual reproduction of 'Fisrolav' was accomplished when vegetative cuttings were taken from the initial selection in the fall of 1999, in a controlled environment in Moncarapacho, Portugal, by, or under the supervision of, Angelika Utecht.

Horticultural examination of plants grown from cuttings of the plant initiated in May 2000 in Hillscheid, Federal Republic of Germany, and continuing thereafter, has demonstrated that the combination of characteristics as herein disclosed for 'Fisrolav' are firmly fixed and are retained through successive generations of asexual reproduction.

BRIEF SUMMARY OF THE INVENTION

'Fisrolav' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fisrolav' in combination distinguish this geranium as a new and distinct cultivar:

1. Lavender-pink and white, semi-double flowers;
2. Medium to large inflorescences, high above the foliage;
3. Medium-green foliage with weak zonation;
4. Vigorous growth, but well-branched plant habit; and
5. medium to late spring flowering response.

Of the many commercial cultivars known to the present inventor, the most similar in comparison to 'Fisrolav' is the variety 'Fiseyely' (U.S. Plant Pat. No. 13,246).

In comparison to 'Fiseyely', the main flower color of flower of 'Fisrolav' is somewhat more to the pink side, and it lacks the red-purple eyes on petals. Furthermore, inflorescences of 'Fisrolav' are higher above the foliage, and plant habit is generally somewhat wider.

BRIEF DESCRIPTION OF THE DRAWING

The accompanying photographic drawing shows typical flower and foliage characteristics of 'Fisrolav' with colors being as true as possible with an illustration of this type. The photographic drawing shows a flowering potted plant of 'Fisrolav'.

DETAILED BOTANICAL DESCRIPTION

The measurements were taken in Hillscheid, Germany, in mid May, 11 weeks after planting of rooted cuttings. The plants were growing in 14-cm pots, they had not been pinched.

In the following description color references are made to The Royal Horticultural Society Color Chart. The color values were determined indoors from plants growing in a green-house in May 2003 in Hillscheid, Germany.

INFLORESCENCE

Umbel:

*Shape.*—Semi-spherical.

*Average diameter.*—110 mm.

*Average depth.*—65–70 mm.

*Peduncle length.*—245 mm, diameter 4–4.5 mm.

*Peduncle color.*—Light green, RHS 143 B, outdoors a slight tinge of brown may occur, approximately RHS 180 D, weak.

*Pedicel.*—36 mm in length.

*Pedicel color.*—Dark red, RHS 181 A.

*Total number of flowers and buds per umbel.*—About 50–80.

Corolla:

*Average diameter.*—50.5 mm.

*Form.*—Semi-double-type.

*Shape.*—Flat cup-shape, with a gap between upper and lower petals.

*Number of petals.*—6–7.

*Shape of petals.*—Obovate, base acute or attenuate, upper end is rounded, margin is entire, but somewhat wavy.

*Size of petals.*—Upper petals: 22–24 mm long, 18–19 mm wide; lower petals: 21–22 mm long, 21–22 mm wide.

*Petaloids.*—0 or 1 in number, same color as the petals, narrower than the petals, almost threadlike.

*Color (general tonality from a distance of three meters).*—Lavender, with a tinge of pink, and with white eyes.

*Color of upper petals.*—Main part approximately RHS 73 A.

*Markings of upper petals.*—Lower part, about one third of the length: white, RHS 155 D, interspersed with fine pink veins RHS 66 C.

*Color of lower petals.*—RHS 73 A.

*Markings of lower petals.*—Absent.

*Color of lower surface of petals.*—RHS 75 B near margin, RHS 75 D in the main part.

*Color of sepals.*—Outer surface: light green, RHS 144 A; inner surface: light green, RHS 144 B.

*Number of sepals.*—5.

*Shape of sepals.*—Linear to lanceolate, acute tip, sessile (base), surface with very weak pubescence, margin entire.

*Size of sepals.*—12–14 mm long, 4 mm wide for the largest upper sepal, 2–3 mm in width for the other sepals.

Bud: (just prior to petals unfolding):

*Shape.*—Elliptical, relatively narrow.

*Color of sepals.*—Light green, RHS 143 C.

*Color of petals.*—RHS 66 C.

*Length.*—19 mm.

*Width.*—9 mm.

Reproductive organs:

*Androecium.*—5–7 fertile anthers, plenty pollen, yellow-orange, RHS 30 A, filaments white, RHS 155 D, to light-pink, RHS 52 D.

*Gynoecium.*—One pistil, reddish style and stigma, RHS 53 C, stigma 5–6 lobed.

*Fertility/seed set.*—Not observed.

Spring flowering response period: In Hillscheid, Germany, in 2001 plants had on average 0.5 flowers opened 8 weeks after planting of rooted cuttings.

Outdoor flower production: Continuously and rich flowering, the flower count in 2003, in Hillscheid, Germany, indicated about 2–2.5 inflorescence per plant in mid May.

Durability: Good stability of flower color, good rain resistance.

Lastingness of the individual flower: About 7–8 days at 18° C., about 15 days for the umbel.

Fragrance: None.

PLANT

Foliage:

*Shape.*—Kidney-shaped, with cordate base, with the gap between the lowest lobes mostly closed, apex rounded with weak lobes.

*Margin.*—Bi-crenated, distinctly wavy.

*Texture.*—Upper surface smooth, dull.

*Size of leaf.*—117 mm wide, 63 mm long.

*Color of upper surface.*—Medium green, approximately RHS 137 C.

*Color of zonation.*—Brown, about RHS 166 A.

*Color of lower surface.*—RHS 137 D.

*Petioles.*—Approximately 70 mm long, 3 mm diameter, green in color, approximately RHS 137 D.

General appearance and form:

*Stem color.*—Green, RHS 143 A to 143 B.

*Internode length.*—40–50 mm.

*Branching pattern.*—5–6 branches.

*Size of plants.*—20.5 cm tall, 36.8 cm wide (11-week-old plants, as described, measured from the top of the soil (base of the main stem) to the surface of the foliage canopy, without inflorescences).

I claim:

1. A new and distinct cultivar of geranium plant named 'Fisrolav', as described and illustrated herein.

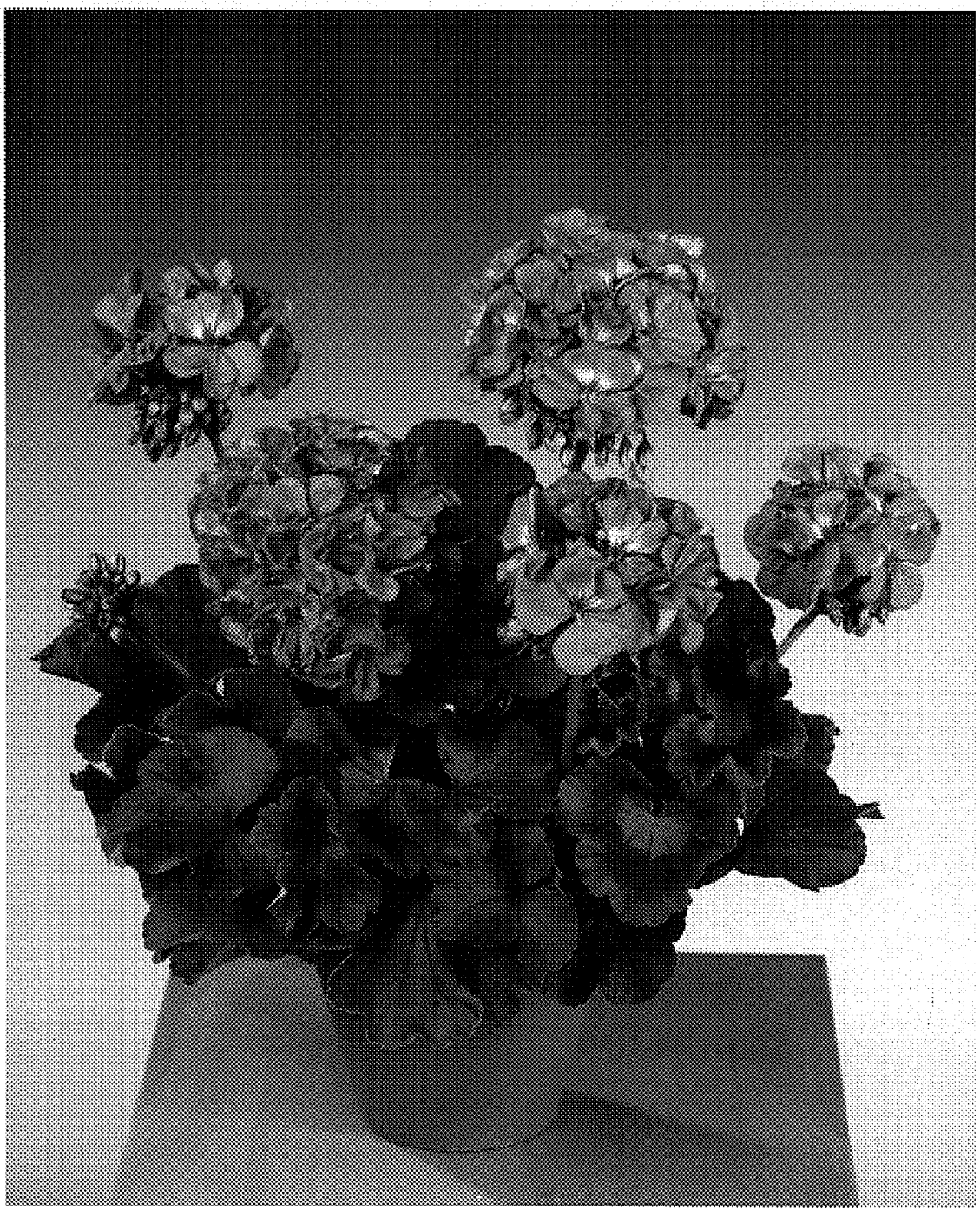

* * * * *